United States Patent
Agapiou et al.

(10) Patent No.: US 8,404,612 B2
(45) Date of Patent: Mar. 26, 2013

(54) CATALYST COMPOSITIONS AND METHODS OF MAKING AND USING THE SAME

(75) Inventors: Agapios K. Agapiou, Humble, TX (US); Jeevan S. Abichandani, Houston, TX (US)

(73) Assignee: Univation Technologies, LLC, Houston, TX (US)

( * ) Notice: Subject to any disclaimer, the term of this patent is extended or adjusted under 35 U.S.C. 154(b) by 0 days.

(21) Appl. No.: 13/549,111

(22) Filed: Jul. 13, 2012

(65) Prior Publication Data

US 2012/0277092 A1 Nov. 1, 2012

Related U.S. Application Data

(62) Division of application No. 13/119,334, filed as application No. PCT/US2009/059216 on Oct. 1, 2009, now Pat. No. 8,247,588.

(60) Provisional application No. 61/195,190, filed on Oct. 3, 2008.

(51) Int. Cl.
*C08F 4/642* (2006.01)
*C08F 4/6592* (2006.01)
*B01J 31/22* (2006.01)

(52) U.S. Cl. ........ 502/132; 502/103; 502/152; 526/154; 526/155; 526/160; 526/943

(58) Field of Classification Search ................. 502/103, 502/132, 152; 526/154, 155, 160, 943
See application file for complete search history.

(56) References Cited

U.S. PATENT DOCUMENTS

| | | |
|---|---|---|
| 5,283,278 A | 2/1994 | Daire et al. |
| 5,795,838 A | 8/1998 | Tsutsui et al. |
| 6,300,436 B1 | 10/2001 | Agapiou et al. |
| 6,593,267 B2 | 7/2003 | Kuo et al. |
| 6,660,815 B2 | 12/2003 | Agapiou et al. |
| 6,680,276 B2 | 1/2004 | Kuo et al. |
| 7,323,526 B2 | 1/2008 | Agapiou et al. |

FOREIGN PATENT DOCUMENTS

| | | |
|---|---|---|
| FR | 2245687 | 4/1975 |
| GB | 1469531 | 4/1977 |
| WO | WO 00/02930 | 1/2000 |
| WO | WO 2009/088428 | 7/2009 |

*Primary Examiner* — Caixia Lu
(74) *Attorney, Agent, or Firm* — Kristina Leavitt; Jennifer A. Schmidt

(57) ABSTRACT

Catalyst compositions for the polymerization of olefins having improved flowability properties are provided.

10 Claims, 2 Drawing Sheets

CATALYST COMPOSITIONS AND METHODS OF MAKING AND USING THE SAME

CROSS-REFERENCE TO RELATED APPLICATIONS

This application is a divisional application of U.S. application Ser. No. 13/119,334 filed Apr. 7, 2011 which is a National Stage Application of International No. PCT/US2009/059216, filed Oct. 1, 2009, that claims the benefit of Ser. No. 61/195,190, filed Oct. 3, 2008, the disclosures of which are incorporated by reference in their entireties.

FIELD OF THE INVENTION

The invention generally relates to catalyst compositions for the polymerization of olefins having improved flowability properties.

BACKGROUND

Metallocene catalysts are widely used to produce polyolefin polymers such as polyethylene polymers. They have provided efficient processes and a variety of new and improved polymers. While there are many advantages to using metallocene catalysts in olefin polymerizations, there remain significant challenges. For example, metallocene catalysts, in particular supported metallocene catalysts, may have poor flowability and the catalyst particles tend to adhere to surfaces or form agglomerates. Adding other reagents to the catalyst composition such as commonly known antifouling agents or continuity additives/aids may compound the flowability issue. This causes practical problems in storing, transporting, and then delivering the dry catalyst into a polymerization reactor. There have been some attempts to address these issues.

In order to address reactor fouling problems caused by high activity metallocene catalysts, other additives such as carboxylate metal salts are often added to the catalyst, either separately or as part of the supported catalyst composition, such as in U.S. Pat. Nos. 6,300,436 and 5,283,278. However, such additives may compound the problem of the flowability of the catalyst.

The flowability problems associated with supported metallocene catalysts have been addressed in various ways. U.S. Pat. No. 5,795,838 is directed to metallocene halides, i.e., those metallocenes having at least one halide leaving group bound to the metal center. To address the flowability issue, the patent directs using a catalyst having certain levels of alkyl groups associated with the benzene-insoluble alkylalumoxanes used to form the supported catalyst compositions, and further, by prepolymerizing the catalyst prior to using it as a dry catalyst. U.S. Pat. Nos. 6,680,276 and 6,593,267 disclose heating the catalyst composition before or while combining it with the carboxylate metal salts. U.S. Pat. No. 6,660,815 discloses the use of a composition of carboxylate metal salt with a flow improver in combination with a polymerization catalyst to improve the flowability and bulk density of the catalyst. U.S. Pat. No. 7,323,526 discloses a supported catalyst composition having improved flow properties wherein the supported catalyst composition comprises an alkylalumoxane, a metallocene-alkyl, an inorganic oxide support having an average particle size of from 0.1 to 50 µm and is calcined at a temperature greater than 600° C., and optionally contains an antifoulant agent. PCT Publication WO 2009/088428, filed Jan. 7, 2008, discloses cooling the catalyst feeding system to maintain adequate catalyst flow.

In light of these attempts to address catalyst system flowability problems, challenges remain, especially at operating temperatures above about 25° C., and particularly above about 30° C.

Thus, it would be advantageous to have an improved catalyst system or composition that flows more easily at elevated temperatures, for example, above about 25° C. and 30° C., and, optionally, is capable of operating in a polymerization process continuously with enhanced reactor operability.

SUMMARY

The invention is directed to catalyst compositions for the polymerization of olefins having improved flowability properties. In a class of embodiments, the invention also relates to a catalyst composition comprising a metallocene catalyst compound and a metal carboxylate salt having improved flow properties and, optionally, is capable of operating in a polymerization process continuously with enhanced reactor operability without the need to cool the feeding system. The invention is additionally directed to a method of making the catalyst composition and to a polymerization process for the production of an ethylene alpha-olefin copolymer.

In one embodiment, the invention provides for a catalyst composition comprising a metallocene catalyst compound and a metal carboxylate salt wherein the catalyst composition at a temperature of 25° C. or higher flows through a funnel in less than 45 seconds, more preferably less than 10 seconds, more preferably less than 5 seconds, wherein the funnel is a glass funnel having a conical mouth with an opening angle of 60 degrees, a hole of 7 mm diameter at the bottom and the funnel has no stem. In another embodiment, the invention provides for a catalyst composition comprising a metallocene catalyst compound and a metal carboxylate salt wherein the catalyst composition at a temperature of 30° C. or higher flows through a funnel in less than 45 seconds, more preferably less than 10 seconds, more preferably less than 5 seconds, wherein the funnel is a glass funnel having a conical mouth with an opening angle of 60 degrees, a hole of 7 mm diameter at the bottom and the funnel has no stem. In another embodiment, the catalyst composition comprises a metallocene catalyst compound and a metal carboxylate salt wherein 20 g of the catalyst composition at a temperature of 25° C. or higher flows through a funnel in less than 10 seconds, wherein the funnel is a glass funnel having a conical mouth with an opening angle of 60 degrees, a hole of 10 mm diameter at the bottom, and the funnel has no stem. In another embodiment, the catalyst composition flows through a funnel in less than 5 seconds, wherein the funnel is a glass funnel having a conical mouth with an opening angle of 60 degrees, a hole of 12 mm diameter at the bottom, and the funnel has no stem. In another embodiment, the catalyst composition, at a temperature of 30° C. or higher, flows through a funnel in less than 45 seconds, wherein the funnel is a glass funnel having a conical mouth with an opening angle of 60 degrees, a hole of 7 mm diameter at the bottom and the funnel is further characterized in having no stem. In another embodiment, the invention is directed to a method of making a catalyst composition comprising a metallocene catalyst compound and a metal carboxylate salt wherein the catalyst composition at a temperature of 25° C. or higher flows through a funnel in less than 45 seconds, wherein the funnel is a glass funnel having a conical mouth with an opening angle of 60 degrees, a hole of 7 mm diameter at the bottom and the funnel is further has no stem.

In yet another embodiment, the invention provides for a metal carboxylate salt composition represented by the formula: MQ x(OOCR)y where M is a Group 2 or Group 13 metal from the Periodic table of Elements; Q is a halogen, hydroxy, alkyl, alkoxy, aryloxy, siloxy, silane or sulfonate group; R is a hydrocarbyl radical having from 14 to 100 carbon atoms; x is an integer from 0 to 3; y is an integer from 1 to 4; and the sum of x and y is equal to the valence of the metal M; wherein the carboxylate salt composition contains a hexane extractable fraction having a peak melting point in a DSC experiment of 60° C. or higher.

In another embodiment, the invention relates to a polymerization process for the production of an ethylene alpha-olefin copolymer comprising: polymerizing ethylene and an alpha-olefin in the presence of a catalyst composition the catalyst composition comprising a metallocene catalyst compound and a metal carboxylate salt wherein the catalyst composition at a temperature of 25° C. or higher flows through a funnel in less than 45 seconds, wherein the funnel is a glass funnel having a conical mouth with an opening angle of 60 degrees, a hole of 7 mm diameter at the bottom and the funnel has no stem.

DETAILED DESCRIPTION

Figure 1:
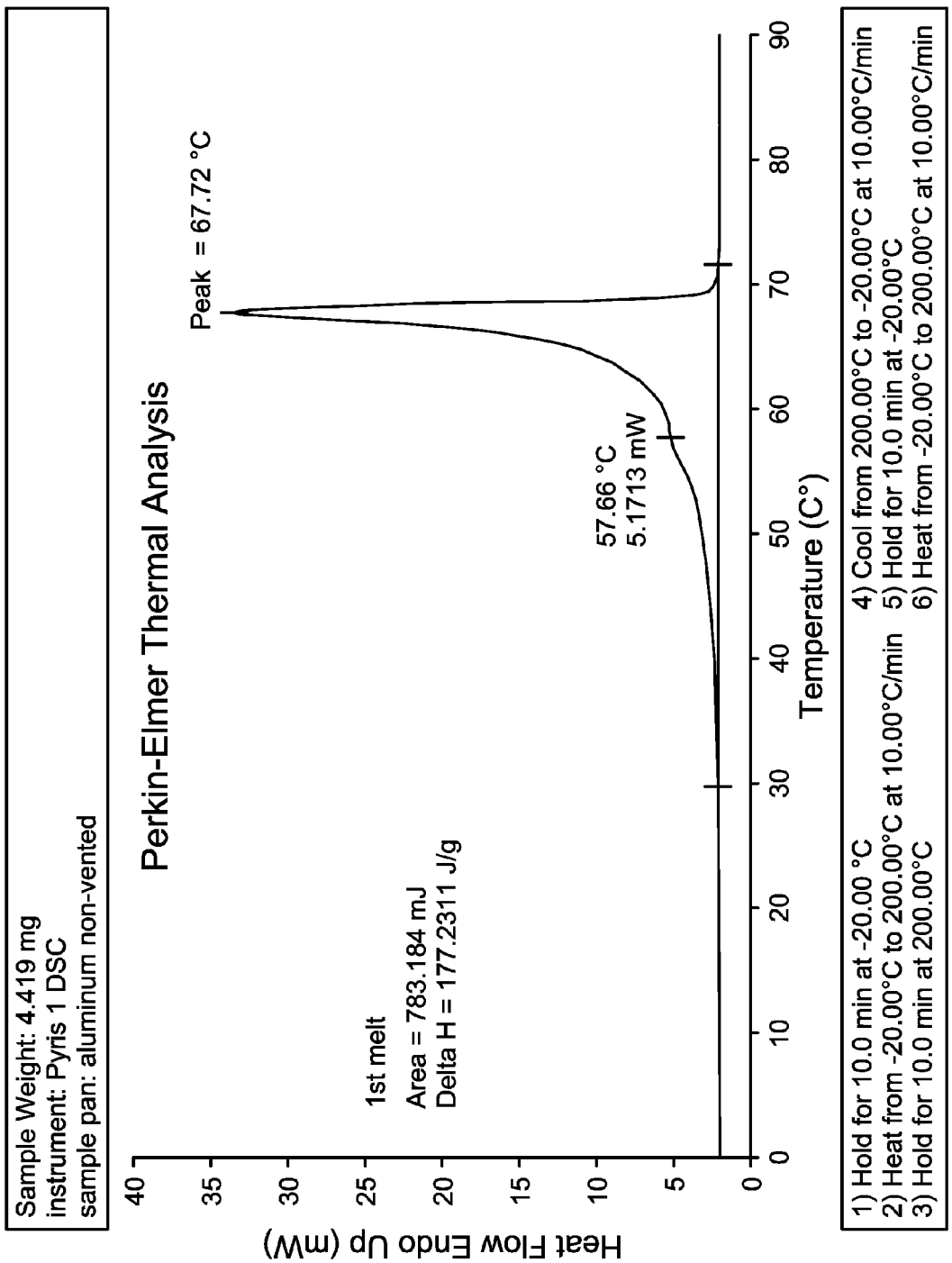
FIG. 1 presents differential scanning calorimetry results for the hexane extractable fraction of an inventive continuity additive as described more in the Examples below.

Before the present compounds, components, compositions, and/or methods are disclosed and described, it is to be understood that unless otherwise indicated this invention is not limited to specific compounds, components, compositions, reactants, reaction conditions, ligands, metallocene structures, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified. Thus, for example, reference to "a leaving group" as in a moiety "substituted with a leaving group" includes more than one leaving group, such that the moiety may be substituted with two or more such groups. Similarly, reference to "a halogen atom" as in a moiety "substituted with a halogen atom" includes more than one halogen atom, such that the moiety may be substituted with two or more halogen atoms, reference to "a substituent" includes one or more substituents, reference to "a ligand" includes one or more ligands, and the like.

As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The invention is directed to catalyst compositions for the polymerization of olefins having improved flowability properties. In a class of embodiments, the invention also relates to a catalyst composition comprising a metallocene catalyst compound and a metal carboxylate salt having improved flow properties and, optionally, is capable of operating in a polymerization process continuously with enhanced reactor operability without the need to cool the feeding system. The invention is additionally directed to a method of making the catalyst composition and to a polymerization process for the production of an ethylene alpha-olefin copolymer.

In several of the embodiments disclosed herein, it has been discovered that using a modified carboxylate metal salt in combination with a catalyst system results in substantially improved flowability of the catalyst system. In particular, utilizing the polymerization catalyst systems described below in combination with the modified carboxylate metal salt results in a substantial improvement in catalyst flowability at temperatures, for example, above 25° C., and especially above about 30° C., while, optionally, retaining at least one of good process operability, catalyst performance, and the capability to produce a broad range of ethylene alpha-olefin polymers.

Metallocene Catalysts

The catalyst system may include at least one metallocene catalyst component. As used herein, "catalyst system" may refer to the catalyst, for example, metallocene catalyst as described herein, and at least one co-catalyst or sometimes called an activator, with optional components, such as supports, additives, such as, for example, continuity additives/aids, scavengers, etc.

The metallocene catalyst or metallocene component may include "half sandwich," (i.e., at least one ligand) and "full sandwich," (i.e., at least two ligands) compounds having one or more Cpo ligands (cyclopentadienyl and ligands isolobal to cyclopentadienyl) bound to at least one Group 3 to Group 12 metal atom, and one or more leaving group(s) bound to the at least one metal atom. Hereinafter, these compounds will be referred to as "metallocene(s)" or "metallocene catalyst component(s)."

In one aspect, the one or more metallocene catalyst components are represented by the formula (I):

$$Cp^A Cp^B MX_n \qquad (I)$$

The metal atom "M" of the metallocene catalyst compound, as described throughout the specification and claims, may be selected from the group consisting of Groups 3 through 12 atoms and lanthanide Group atoms in one embodiment; and selected from the group consisting of Groups 4, 5 and 6 atoms in yet a more particular embodiment, and a Ti, Zr, Hf atoms in yet a more particular embodiment, and Zr in yet a more particular embodiment. The groups bound the metal atom "M" is such that the compounds described below in the formulas and structures are neutral, unless otherwise indicated. The Cp ligand(s) form at least one chemical bond with the metal atom M to form the "metallocene catalyst compound". The Cp ligands are distinct from the leaving groups bound to the catalyst compound in that they are not highly susceptible to substitution/abstraction reactions.

M is as described above; each X is chemically bonded to M; each Cp group is chemically bonded to M; and n is 0 or an integer from 1 to 4, and either 1 or 2 in a particular embodiment.

The ligands represented by $Cp^A$ and $Cp^B$ in formula (I) may be the same or different cyclopentadienyl ligands or ligands isolobal to cyclopentadienyl, either or both of which may contain heteroatoms and either or both of which may be substituted by a group R. In one embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (I) may be unsubstituted or substituted with any one or combination of substituent groups R. Non-limiting examples of substituent groups R as used in formula (I) include hydrogen radicals, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof.

More particular non-limiting examples of alkyl substituents R associated with formula (I) includes methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like. Other possible radicals include substituted alkyls and aryls such as, for example, fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins such as but not limited to olefinically unsaturated substituents including vinyl-terminated ligands, for example 3-butenyl, 2-propenyl, 5-hexenyl and the like. In one embodiment, at least two R groups, two adjacent R groups in one embodiment, are joined to form a ring structure having from 3 to 30 atoms selected from the group consisting of carbon, nitrogen, oxygen, phosphorous, silicon, germanium, aluminum, boron and combinations thereof. Also, a substituent group R group such as 1-butanyl may form a bonding association to the element M.

Each X in formula (I) is independently selected from the group consisting of: any leaving group in one embodiment; halogen ions, hydrides, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, X is $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment.

In another aspect, the metallocene catalyst component includes those of formula (I) where $Cp^A$ and $Cp^B$ are bridged to each other by at least one bridging group, (A), such that the structure is represented by formula (II):

$$Cp^A(A)Cp^B MX_n \qquad (II)$$

These bridged compounds represented by formula (II) are known as "bridged metallocenes". $Cp^A$, $Cp^B$, M, X and n are as defined above for formula (I); and wherein each Cp ligand is chemically bonded to M, and (A) is chemically bonded to each Cp. Non-limiting examples of bridging group (A) include divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, divalent thioethers. Additional non-limiting examples of bridging group (A) include divalent hydrocarbon groups containing at least one Group 13 to 16 atom, such as but not limited to at least one of a carbon, oxygen, nitrogen, silicon, aluminum, boron, germanium and tin atom and combinations thereof; wherein the heteroatom may also be $C_1$ to $C_{12}$ alkyl or aryl substituted to satisfy neutral valency. The bridging group (A) may also contain substituent groups R as defined above for formula (I) including halogen radicals and iron. More particular non-limiting examples of bridging group (A) are represented by $C_1$ to $C_6$ alkylenes, substituted $C_1$ to $C_6$ alkylenes, oxygen, sulfur,  (wherein "=" represents two chemical bonds), where R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In one embodiment, the bridged metallocene catalyst component of formula (II) has two or more bridging groups (A).

Other non-limiting examples of bridging group (A) include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis (trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

In another embodiment, bridging group (A) may also be cyclic, comprising, for example 4 to 10, 5 to 7 ring members in a more particular embodiment. The ring members may be selected from the elements mentioned above, from one or more of B, C, Si, Ge, N and O in a particular embodiment. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O, in particular, Si and Ge. The bonding arrangement between the ring and the Cp groups may be either cis-, trans-, or a combination.

The cyclic bridging groups (A) may be saturated or unsaturated and/or carry one or more substituents and/or be fused to one or more other ring structures. If present, the one or more substituents are selected from the group consisting of hydrocarbyl (e.g., alkyl such as methyl) and halogen (e.g., F, Cl) in one embodiment. The one or more Cp groups which the above cyclic bridging moieties may optionally be fused to may be saturated or unsaturated and are selected from the group consisting of those having 4 to 10, more particularly 5, 6 or 7 ring members (selected from the group consisting of C, N, O and S in a particular embodiment) such as, for example, cyclopentyl, cyclohexyl and phenyl. Moreover, these ring structures may themselves be fused such as, for example, in the case of a naphthyl group. Moreover, these (optionally fused) ring structures may carry one or more substituents. Illustrative, non-limiting examples of these substituents are hydrocarbyl (particularly alkyl) groups and halogen atoms.

The ligands $Cp^A$ and $Cp^B$ of formula (I) and (II) are different from each other in one embodiment, and the same in another embodiment.

In yet another aspect, the metallocene catalyst components include mono-ligand metallocene compounds (e.g., mono cyclopentadienyl catalyst components) such as described in WO 93/08221 for example which is incorporated herein by reference.

In yet another aspect, the at least one metallocene catalyst component is an unbridged "half sandwich" metallocene represented by the formula (IV):

$$Cp^A MQ_q X_n \qquad (IV)$$

wherein $Cp^A$ is defined as for the Cp groups in (I) and is a ligand that is bonded to M; each Q is independently bonded to M; Q is also bound to $Cp^A$ in one embodiment; X is a leaving group as described above in (I); n ranges from 0 to 3, and is 1 or 2 in one embodiment; q ranges from 0 to 3, and is 1 or 2 in one embodiment. In one embodiment, $Cp^A$ is selected from the group consisting of cyclopentadienyl, indenyl, tetrahydroindenyl, fluorenyl, substituted version thereof, and combinations thereof.

In formula (IV), Q is selected from the group consisting of ROO⁻, RO—, R(O)—, —NR—, —CR$_2$—, —S—, —NR$_2$, —CR$_3$, —SR, —SiR$_3$, —PR$_2$, —H, and substituted and unsubstituted aryl groups, wherein R is selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, R is selected from $C_1$ to $C_6$ alkyls, $C_6$ to $C_{12}$ aryls, $C_1$ to $C_6$ alkylamines, $C_6$ to $C_{12}$ alkylarylamines, $C_1$ to $C_6$ alkoxys, $C_6$ to $C_{12}$ aryloxys, and the like. Non-limiting examples of Q include $C_1$ to $C_{12}$ carbamates, $C_1$ to $C_{12}$ carboxylates (e.g., pivalate), $C_2$ to $C_{20}$ alkyls, and $C_2$ to $C_{20}$ heteroallyl moieties.

Described another way, the "half sandwich" metallocenes above can be described as in formula (II), such as described in, for example, U.S. Pat. No. 6,069,213:

$$Cp^A M(Q_2 GZ)X_n \text{ or } T(Cp^A M(Q_2 GZ)X_n)_m \qquad (V)$$

wherein M, $Cp^A$, X and n are as defined above;

$Q_2GZ$ forms a polydentate ligand unit (e.g., pivalate), wherein at least one of the Q groups form a bond with M, and is defined such that each Q is independently selected from the group consisting of —O—, —NR—, —CR$_2$— and —S—; G is either carbon or silicon; and Z is selected from the group consisting of R, —OR, —NR$_2$, —CR$_3$, —SR, —SiR$_3$, —PR$_2$, and hydride, providing that when Q is —NR—, then Z is selected from the group consisting of —OR, —NR$_2$, —SR, —SiR$_3$, —PR$_2$; and provided that neutral valency for Q is satisfied by Z; and wherein each R is independently selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In another embodiment, R is selected from the group consisting of $C_1$ to $C_{10}$ heteroatom containing groups, $C_1$ to $C_{10}$ alkyls, $C_6$ to $C_{12}$ aryls, $C_6$ to $C_{12}$ alkylaryls, $C_1$ to $C_{10}$ alkoxys, and $C_6$ to $C_{12}$ aryloxys;

n is 1 or 2 in a particular embodiment; and

T is a bridging group selected from the group consisting of $C_1$ to $C_{10}$ alkylenes, $C_6$ to $C_{12}$ arylenes and $C_1$ to $C_{10}$ heteroatom containing groups, and $C_6$ to $C_{12}$ heterocyclic groups; wherein each T group bridges adjacent "$Cp^A M(Q_2 GZ)X_n$" groups, and is chemically bonded to the $Cp^A$ groups.

m is an integer from 1 to 7; m is an integer from 2 to 6 in a more particular embodiment.

In another aspect, the at least one metallocene catalyst component can be described more particularly in structures (VIa), (VIb), (VIc), (VId), (VIe), and (VIf):

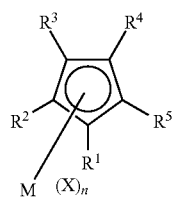
(VIa-i)

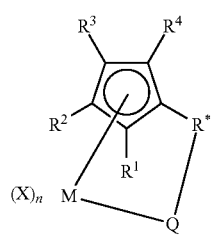
(VIa-ii)

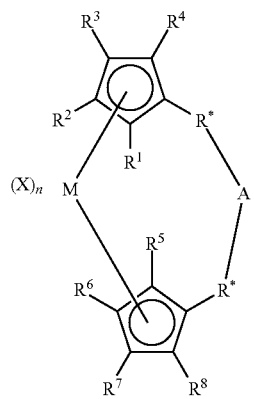
(VIb)

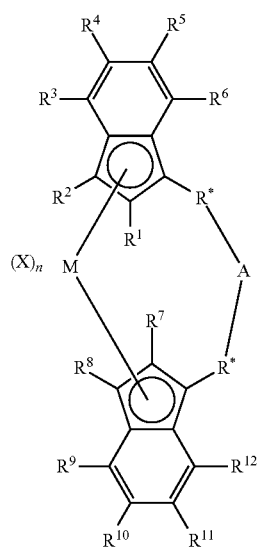
(VIc)

-continued

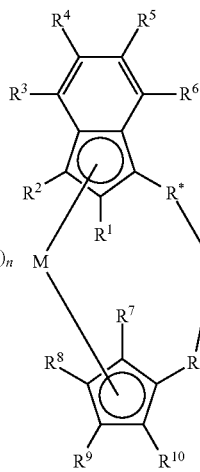
(VId)

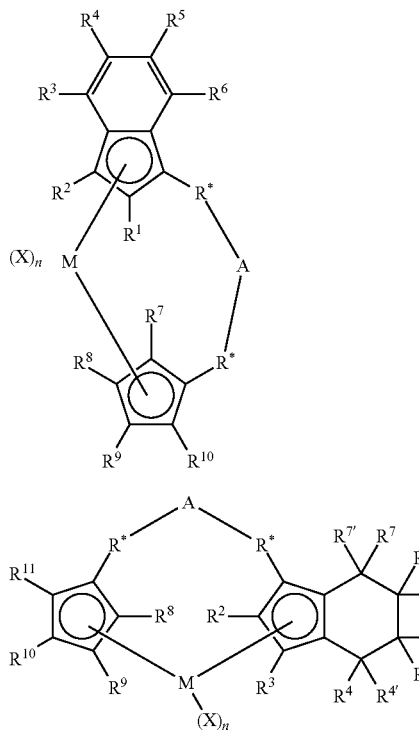
(VIe)

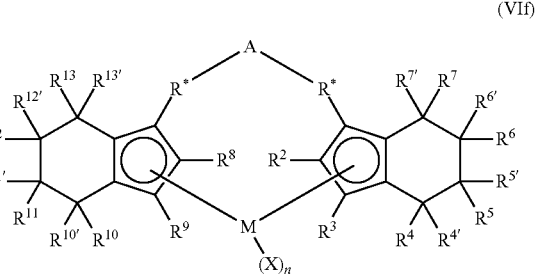
(VIf)

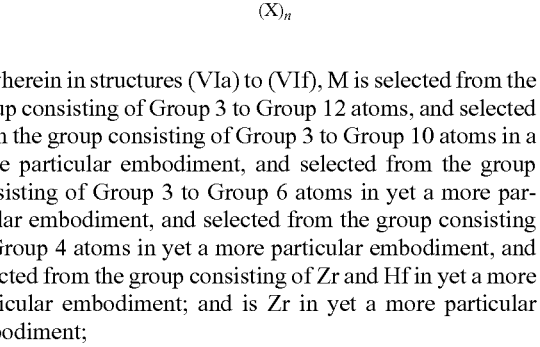

wherein in structures (VIa) to (VIf), M is selected from the group consisting of Group 3 to Group 12 atoms, and selected from the group consisting of Group 3 to Group 10 atoms in a more particular embodiment, and selected from the group consisting of Group 3 to Group 6 atoms in yet a more particular embodiment, and selected from the group consisting of Group 4 atoms in yet a more particular embodiment, and selected from the group consisting of Zr and Hf in yet a more particular embodiment; and is Zr in yet a more particular embodiment;

wherein Q in (VIa) to (VIf) is selected from the group consisting of hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos, alkylenes, aryls, arylenes, alkoxys, aryloxys, amines, arylamines (e.g., pyridyl) alkylamines, phosphines, alkylphosphines, substituted alkyls, substituted aryls, substituted alkoxys, substituted aryloxys, substituted amines, substituted alkylamines, substituted phosphines, substituted alkylphosphines, carbamates, heteroallyls, carboxylates (non-limiting examples of suitable carbamates and carboxylates include trimethylacetate, trimethylacetate, methylacetate, p-toluate, benzoate, diethylcarbamate, and dimethylcarbamate), fluorinated alkyls, fluorinated aryls, and fluorinated alkylcarboxylates; wherein the saturated groups defining Q comprise from 1 to 20 carbon atoms in one embodiment; and wherein the aromatic groups comprise from 5 to 20 carbon atoms in one embodiment; wherein R* may be selected from divalent alkyls, divalent lower alkyls, divalent substituted alkyls, divalent heteroalkyls, divalent alkenyls, divalent lower alkenyls, divalent substituted alkenyls, divalent heteroalkenyls, divalent alkynyls, divalent lower alkynyls, divalent substituted alkynyls, divalent heteroalkynyls, divalent alkoxys, divalent lower alkoxys, divalent aryloxys, divalent alkylthios, divalent lower alkyl thios, divalent arylthios, divalent aryls, divalent substituted aryls, divalent heteroaryls, divalent aralkyls, divalent aralkylenes, divalent alkaryls, divalent alkarylenes, divalent haloalkyls, divalent haloalkenyls, divalent haloalkynyls, divalent heteroalkyls, divalent heterocycles, divalent heteroaryls, divalent heteroatom-containing groups, divalent hydrocarbyls, divalent lower hydrocarbyls, divalent substituted hydrocarbyls, divalent heterohydrocarbyls, divalent silyls, divalent boryls, divalent phosphinos, divalent phosphines, divalent aminos, divalent amines, divalent ethers, divalent thioethers. Additionally, R* may be from the group of divalent hydrocarbylenes and heteroatom-containing hydrocarbylenes in one embodiment; and selected from the group consisting of alkylenes, substituted alkylenes and heteroatom-containing hydrocarbylenes in another embodiment; and selected from the group consisting of $C_1$ to $C_{12}$ alkylenes, $C_1$ to $C_{12}$ substituted alkylenes, and $C_1$ to $C_{12}$ heteroatom-containing hydrocarbylenes in a more particular embodiment; and selected from the group consisting of $C_1$ to $C_4$ alkylenes in yet a more particular embodiment; and wherein both R* groups are identical in another embodiment in structures (VIf);

A is as described above for (A) in structure (II), and more particularly, selected from the group consisting of a chemical bond, —O—, —S—, —$SO_2$—, —NR—, =$SiR_2$, =$GeR_2$, =$SnR_2$, —$R_2SiSiR_2$—, RP=, $C_1$ to $C_{12}$ alkylenes, substituted $C_1$ to $C_{12}$ alkylenes, divalent $C_4$ to $C_{12}$ cyclic hydrocarbons and substituted and unsubstituted aryl groups in one embodiment; and selected from the group consisting of $C_5$ to $C_8$ cyclic hydrocarbons, —$CH_2CH_2$—, =$CR_2$ and =$SiR_2$ in a more particular embodiment; wherein and R is selected from the group consisting of alkyls, cycloalkyls, aryls, alkoxys, fluoroalkyls and heteroatom-containing hydrocarbons in one embodiment; and R is selected from the group consisting of $C_1$ to $C_6$ alkyls, substituted phenyls, phenyl, and $C_1$ to $C_6$ alkoxys in a more particular embodiment; and R is selected from the group consisting of methoxy, methyl, phenoxy, and phenyl in yet a more particular embodiment; wherein A may be absent in yet another embodiment, in which case each R* is defined as for $R^1$-$R^{13}$; each X is as described above in (I); n is an integer from 0 to 4, and from 1 to 3 in another embodiment, and 1 or 2 in yet another embodiment; and $R^1$ through $R^{13}$ are independently: selected from the group consisting of hydrogen radicals, hydrocarbyls, lower hydrocarbyls, substituted hydrocarbyls, heterohydrocarbyls, alkyls, lower alkyls, substituted alkyls, heteroalkyls, alkenyls, lower alkenyls, substituted alkenyls, heteroalkenyls, alkynyls, lower alkynyls, substituted alkynyls, heteroalkynyls, alkoxys, lower alkoxys, aryloxys, hydroxyls, alkylthios, lower alkyls thios, arylthios, thioxys, aryls, substituted aryls, heteroaryls, aralkyls, aralkylenes, alkaryls, alkarylenes, halides, haloalkyls, haloalkenyls, haloalkynyls, heteroalkyls, heterocycles, heteroaryls, heteroatom-containing groups, silyls, boryls, phosphinos, phosphines, aminos, amines, cycloalkyls, acyls, aroyls, alkylthiols, dialkylamines, alkylamidos, alkoxycarbonyls, aryloxycarbonyls, carbomoyls, alkyl- and dialkyl-carbamoyls, acyloxys, acylaminos, aroylaminos through $R^{13}$ may also be selected independently from $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in one embodiment; selected from the group consisting of hydrogen radical, fluorine radical, chlorine radical, bromine radical, $C_1$ to $C_6$ alkyls, $C_2$ to $C_6$ alkenyls, $C_7$ to $C_{18}$ alkylaryls, $C_1$ to $C_6$ fluoroalkyls, $C_2$ to $C_6$ fluoroalkenyls, $C_7$ to $C_{18}$ fluoroalkylaryls in a more particular embodiment; and hydrogen radical, fluorine radical, chlorine radical, methyl, ethyl, propyl, isopropyl, butyl, isobutyl, tertiary butyl, hexyl, phenyl, 2,6-dimethylpheyl, and 4-tertiarybutylpheyl groups in yet a more particular embodiment; wherein adjacent R groups may form a ring, either saturated, partially saturated, or completely saturated.

The structure of the metallocene catalyst component represented by (VIa) may take on many forms such as disclosed in, for example, U.S. Pat. No. 5,026,798, U.S. Pat. No. 5,703,187, and U.S. Pat. No. 5,747,406, including a dimmer or oligomeric structure, such as disclosed in, for example, U.S. Pat. No. 5,026,798 and U.S. Pat. No. 6,069,213.

In a particular embodiment of the metallocene represented in (VId), $R^1$ and $R^2$ form a conjugated 6-membered carbon ring system that may or may not be substituted.

It is contemplated that the metallocene catalysts components described above include their structural or optical or enantiomeric isomers (racemic mixture), and may be a pure enantiomer in one embodiment.

As used herein, a single, bridged, asymmetrically substituted metallocene catalyst component having a racemic and/or meso isomer does not, itself, constitute at least two different bridged, metallocene catalyst components.

The "metallocene catalyst component" may comprise any combination of any "embodiment" described herein.

Metallocene compounds and catalysts are known in the art and any one or more may be utilized herein. Suitable metallocenes include but are not limited to all of the metallocenes disclosed and referenced in the U.S. patents cited above, as well as those disclosed and referenced in U.S. Pat. Nos. 7,179,876, 7,169,864, 7,157,531, 7,129,302, 6,995,109, 6,958,306, 6,884,748, 6,689,847, U.S. Patent Application publication number 2007/0055028, and published PCT Application Nos. WO 97/22635, WO 00/699/22, WO 01/30860, WO 01/30861, WO 02/46246, WO 02/50088, WO 04/026921, and WO 06/019494, all fully incorporated herein by reference. Additional catalysts suitable for use herein include those referenced in U.S. Pat. Nos. 6,309,997, 6,265,338, U.S. Patent Application publication number 2006/019925, and the following articles: Chem Rev 2000, 100, 1253, Resconi; Chem Rev 2003, 103, 283; Chem. Eur. J. 2006, 12, 7546 Mitsui; J Mol Catal A 2004, 213, 141; Macromol Chem Phys, 2005, 206, 1847; and J Am Chem Soc 2001, 123, 6847.

Mixed Catalysts

It is also within the scope of this invention that one or metallocene catalysts as described above can be combined with another type of catalyst compound, such as conventional polyolefin catalysts, as well as Group 15 atom containing catalysts described below.

Group 15 Atom Containing Catalysts

"Group 15 atom containing" catalysts or "Group 15-containing" catalysts may include complexes of Group 3 to 12 metal atoms, wherein the metal atom is 2 to 8 coordinate, the coordinating moiety or moieties including at least two Group 15 atoms, and up to four Group 15 atoms. In one embodiment, the Group 15-containing catalyst component is a complex of a Group 4 metal and from one to four ligands such that the Group 4 metal is at least 2 coordinate, the coordinating moiety or moieties including at least two nitrogens. Representative Group 15-containing compounds are disclosed in, for example, WO 99/01460, EP A10 893 454, U.S. Pat. No. 5,318,935, U.S. Pat. No. 5,889,128, U.S. Pat. No. 6,333,389 B2 and U.S. Pat. No. 6,271,325 B1.

In a class of embodiments, the Group 15-containing catalyst components may include Group 4 imino-phenol complexes, Group 4 bis(amide) complexes, and Group 4 pyridyl-amide complexes that are active towards olefin polymerization to any extent. In one possible embodiment, the Group 15-containing catalyst component may include a bisamide compound such as [(2,3,4,5,6 Me5C6)NCH2CH2] 2NHZrBz2 (from Boulder Chemical).

Activators and Activation Methods for Catalyst Compounds

An activator is defined in a broad sense as any combination of reagents that increases the rate at which a transition metal compound oligomerizes or polymerizes unsaturated monomers, such as olefins. The catalyst compounds according to the invention may be activated for oligomerization and/or polymerization catalysis in any manner sufficient to allow coordination or cationic oligomerization and or polymerization.

Generally, catalysts may contain a formal anionic ligand, such as hydride or hydrocarbyl, with an adjacent (cis) coordination site accessible to an unsaturated monomer. Coordination of an unsaturated monomer to the cis coordination site allows a migratory insertion reaction to form a metal alkyl. Repetition of this process causes the chain growth associated with oligomerization and/or polymerization. An activator is thus any combination of reagents that facilitates formation of a transition metal compound containing cis coordinated olefin and hydride or hydrocarbyl.

When the transition metal compound contains at least one hydride or hydrocarbyl ligand, activation can be achieved by removal of formal anionic or neutral ligand(s), of higher binding affinity than the unsaturated monomer. This removal, also called abstraction, process may have a kinetic rate that is first-order or non-first order with respect to the activator. Activators that remove anionic ligands are termed ionizing activators. Alternatively, activators that remove neutral ligands are termed non-ionizing activators. Activators may be strong Lewis-acids which may play either the role of an ionizing or non-ionizing activator.

When the transition metal compound does not contain at least one hydride or hydrocarbyl ligands, then activation may be a one step or multi step process. One step in this process includes coordinating a hydride or hydrocarbyl group to the metal compound. A separate activation step is removal of anionic or neutral ligands of higher binding affinity than the unsaturated monomer. These activation steps may occur in the presence of an olefin and occur either in series or in parallel. More than one sequence of activation steps is possible to achieve activation.

The activator may also act to coordinate a hydride or hydrocarbyl group to the transition metal compound. When the transition metal compound does not contain at least one hydride or hydrocarbyl ligands but does contain at least one functional group ligand, activation may be effected by substitution of the functional group with a hydride, hydrocarbyl or substituted hydrocarbyl group. This substitution may be effected with appropriate hydride or alkyl reagents of group 1, 2, 12, 13 elements as are known in the art. To achieve activation, it may be necessary to also remove anionic or neutral ligands of higher binding affinity than the unsaturated monomer.

The activator may also act to coordinate a hydride or hydrocarbyl group to the transition metal compound. If the transition metal compound does not contain anionic ligands, then a hydride, hydrocarbyl or substituted hydrocarbyl may be coordinated to a metal using electrophilic proton or alkyl transfer reagents represented by H+(LB)nA-, (R9)+(LB)nA-. R9 may be a hydrocarbyl or a substituted hydrocarbyl; LB is a Lewis-base, and wherein n=0, 1 or 2. Non-limiting examples of preferred Lewis-bases are diethyl ether, dimethyl ether, ethanol, methanol, water, acetonitrile, N,N-dimethylaniline. A- is an anion, preferably a substituted hydrocarbon, a functional group, or a non-coordinating anion. Non-limiting examples of A- may include halides, carboxylates, phosphates, sulfates, sulfonates, borates, aluminates, alkoxides, thioalkoxides, anionic substituted hydrocarbons, anionic metal complexes and the like.

Other activators include those described in WO 98/07515 such as tris (2,2',2"-nonafluorobiphenyl) fluoroaluminate. Combinations of activators are also contemplated by the invention, for example, alumoxanes and ionizing activators in combinations, see for example, EP-B1 0 573 120, WO 94/07928 and WO 95/14044 and U.S. Pat. Nos. 5,153,157 and 5,453,410. WO 98/09996 describes activating metallocene catalyst compounds with perchlorates, periodates and iodates including their hydrates. WO 98/30602 and WO 98/30603 describe the use of lithium (2,2'-bisphenyl-ditrimethylsilicate). 4THF as an activator for a metallocene catalyst compound. WO 99/18135 describes the use of organo-boron-aluminum activators. EP-B1-0 781 299 describes using a silylium salt in combination with a non-coordinating compatible anion. WO 2007/024773 suggests the use of activator-supports which may comprise a chemically-treated solid oxide, clay mineral, silicate mineral, or any combination thereof. Also, methods of activation such as using radiation (see EP-B1-0 615 981), electro-chemical oxidation, and the like are also contemplated as activating methods for the purposes of rendering the neutral metallocene catalyst compound or precursor to a metallocene cation capable of polymerizing olefins. Other activators or methods for activating a metallocene catalyst compound are described in, for example, U.S. Pat. Nos. 5,849,852, 5,859,653 and 5,869,723 and PCT WO 98/32775.

In one embodiment, alumoxanes activators may be utilized as an activator in the catalyst composition of the invention. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

When the activator is an alumoxane (modified or unmodified), some embodiments select the maximum amount of activator at a 5000-fold molar excess Al/M over the catalyst precursor (per metal catalytic site). The minimum activator-to-catalyst-precursor is a 1:1 molar ratio.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in, for example, U.S. Pat. Nos. 4,665, 208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, WO 94/10180 and WO 99/15534. It may be preferable to use a visually clear methylalumoxane. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A, disclosed in U.S. Pat. No. 5,041,584).

Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (see, for example, WO 98/43983), boric acid (see, for example, U.S. Pat. No. 5,942,459) or a combination thereof. It is also within the scope of this invention to use neutral or ionic activators alone or in combination with alumoxane or modified alumoxane activators.

Examples of neutral stoichiometric activators may include tri-substituted boron, tellurium, aluminum, gallium and indium or mixtures thereof. The three substituent groups may be each independently selected from the group of alkyls, alkenyls, halogen, substituted alkyls, aryls, arylhalides, alkoxy and halides. Preferably, the three substituent groups may be independently selected from the group of halogen, mono or multicyclic (including halosubstituted) aryls, alkyls, and alkenyl compounds and mixtures thereof; in a class of embodiments are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). Alternatively, the three groups are alkyls having 1 to 4 carbon groups, phenyl, napthyl or mixtures thereof. In other embodiments, the three groups are halogenated, preferably fluorinated, aryl groups. In yet other illustrative embodiments, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in, for example, European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994.

Supports

As used herein, an "inorganic oxide support" or "support" refers to compounds comprising Group 2, 3, 4, 5, 13 and 14 oxides and chlorides. Preferably support materials include silica, magnesia, titania, zirconia, montmorillonite, phyllosilicate, alumina, silica-alumina, silica-chromium, silica-titania, magnesium chloride, graphite, magnesia, titania, zirconia, montmorillonite, phyllosilicate, and the like. Most preferably, the inorganic oxide support is silica. Supports are well known in the art and described by, for example, G. G. Hlalky, "Heterogeneous Single-Site Catalysts for Olefin Polymerization" in 100(4) CHEMICAL REVIEWS 1347-1374 (2000). Preferably, the inorganic oxide support possesses an average particle size in the range of from 0.1 to 50 µm, and more preferably from 1 to 40 µm, and most preferably from 5 to 40 µm.

Methods for Supporting

The above described catalyst compounds may be combined with one or more support materials using one of the support methods well known in the art or as described below. In one possible embodiment, the method of the invention uses a catalyst, such as a metallocene catalyst, in a supported form. For example, in another embodiment, a catalyst compound is in a supported form, for example, deposited on, contacted with, or incorporated within, adsorbed or absorbed in, or on.

In one embodiment, the support, such as an inorganic oxide, may have a surface area in the range of from about 10 to about 700 m$^2$/g, pore volume in the range of from about 0.1 to about 4.0 cc/g and average particle size in the range of from about 1 to about 500 nm. Alternatively, the surface area of the support may be in the range of from about 50 to about 500 m$^2$/g, pore volume of from about 0.5 to about 3.5 cc/g and average particle size of from about 10 to about 200 nm. In another embodiment, the surface area of the support is in the range is from about 100 to about 400 m$^2$/g, pore volume from about 0.8 to about 3.0 cc/g and average particle size is from about 5 to about 100 nm. In yet another illustrative embodiment, the average pore size of the support is from about 1 to about 50 nm The average pore size of the support of the invention typically has pore size in the range of from 10 to 1000 Å preferably 50 to about 500 Å and most preferably 75 to about 350 Å.

In one embodiment, the catalyst compounds may be supported on the same or separate supports together with an activator, or the activator may be used in an unsupported form, or may be deposited on a support different from the supported catalyst compounds of the invention, or any combination thereof. This may be accomplished by any technique commonly used in the art.

There are various other methods in the art for supporting a polymerization catalyst compound or catalyst system of the invention. For example, the catalyst compound may contain a polymer bound ligand as described in, for example, U.S. Pat. Nos. 5,473,202 and 5,770,755; the catalyst may be spray dried as described in, for example, U.S. Pat. No. 5,648,310; the support used with the catalyst may be functionalized as described in European publication EP-A-0 802 203, or at least one substituent or leaving group is selected as described in U.S. Pat. No. 5,688,880.

Continuity Additives/Aids

As used herein, the term "continuity additive or aid" and "antifoulant agent" refer to compounds or mixtures of compounds, preferably solid or liquid, that are useful in gas phase or slurry phase polymerization processes to reduce or eliminate fouling of the reactor, where "fouling" may be manifested by any number of phenomena including sheeting of the reactor walls, plugging of inlet and outlet lines, formation of large agglomerates, or other forms of reactor upsets known in the art. For purposes here, the terms may be used interchangeably. In a class of embodiments, the antifoulant agent or continuity additive is supported on the inorganic oxide of the supported catalyst composition described herein.

Non-limiting examples include fatty acid amines, amide-hydrocarbon or ethyoxylated-amide compounds such as described as "surface modifiers" in WO 96/11961; carboxylate compounds such as aryl-carboxylates and long chain hydrocarbon carboxylates, and fatty acid-metal complexes; alcohols, ethers, sulfate compounds, metal oxides and other compounds known in the art. Some specific examples of antifouling agents include 1,2-diether organic compounds, magnesium oxide, ARMOSTAT 310, ATMER 163, ATMER AS-990, and other glycerol esters, ethoxylated amines (e.g., N,N-bis(2-hydroxyethyl)octadecylamine), alkyl sulfonates, and alkoxylated fatty acid esters; STADIS 450 and 425, KEROSTAT CE 4009 and KEROSTAT CE 5009. chromium N-oleylanthranilate salts, calcium salts of a Medialan acid and di-tert-butylphenol; POLYFLO 130, TOLAD 511 (a-olefin-acrylonitrile copolymer and polymeric polyamine), EDENOL D32, aluminum stearate, sorbitan-monooleate, glycerol monostearate, methyl toluate, dimethyl maleate, dimethyl furnarate, triethylamine, 3,3-diphenyl-3-(imidazol-1-yl)-propin, and like compounds. In a class of embodiments, a particularly preferred antifoulant agent is a carboxylate metal compound as described below, optionally, with other compounds as described in this section.

Carboxylate Metal Salt

As used herein, the term "carboxylate metal salt" is any mono- or di- or tri-carboxylic acid salt with a metal portion from the Periodic Table of Elements. Non-limiting examples include saturated, unsaturated, aliphatic, aromatic or saturated cyclic carboxylic acid salts. Examples of the carboxylate ligand include, but are not limited to, acetate, propionate, butyrate, valerate, pivalate, caproate, isobuytlacetate, t-butyl-acetate, caprylate, heptanate, pelargonate, undecanoate, oleate, octoate, palmitate, myristate, margarate, stearate, arachate and tercosanoate. Non-limiting examples of the metal portion includes a metal from the Periodic Table of Elements selected from the group of Al, Mg, Ca, Sr, Sn, Ti, V, Ba, Zn, Cd, Hg, Mn, Fe, Co, Ni, Pd, Li and Na.

In one embodiment, the carboxylate metal salt is represented by the following general formula:

$$M(O)x(OOCR)y$$

where M is a metal from Groups 1 to 16 and the Lanthanide and Actinide series, preferably from Groups 1 to 7 and 13 to 16, more preferably from Groups 3 to 7 and 13 to 16, even more preferably Groups 2 and 13, and most preferably Group 13; Q is halogen, hydrogen, a hydroxy or hydroxide, alkyl, alkoxy, aryloxy, siloxy, silane or sulfonate group R is a hydrocarbyl radical having from 2 to 100 carbon atoms, preferably 4 to 50 carbon atoms; and x is an integer from 0 to 3 and y is an integer from 1 to 4 and the sum of x and y is equal to the valence of the metal.

R in the above formula may be the same or different. Non-limiting examples of R include hydrocarbyl radicals having 2 to 100 carbon atoms that include alkyl, aryl, aromatic, aliphatic, cyclic, saturated or unsaturated hydrocarbyl radicals. In an embodiment of the invention, R is a hydrocarbyl radical having greater than or equal to 8 carbon atoms, preferably greater than or equal to 12 carbon atoms and more preferably greater than 14 carbon atoms. In another embodiment R comprises a hydrocarbyl radical having from 17 to 90 carbon atoms, preferably 17 to 72, and most preferably from 17 to 54 carbon atoms.

Non-limiting examples of Q in the above formula include one or more, same or different, hydrocarbon containing group such as alkyl, cycloalkyl, aryl, alkenyl, arylalkyl, arylalkenyl or alkylaryl, alkylsilane, arylsilane, alkylamine, arylamine, alkyl phosphide, alkoxy having from 1 to 30 carbon atoms. The hydrocarbon containing group may be linear, branched, or even substituted. Also, Q in one embodiment is an inorganic group such as a halide, sulfate or phosphate.

In a class of embodiments, carboxylate metal salts may comprise aluminum carboxylates such as aluminum mono, di- and tri-stearates, aluminum octoates, oleates and cyclo-hexylbutyrates. In yet a more preferred embodiment, the carboxylate metal salt comprises $(CH_3(CH_2)_{16}COO)_3$ Al, an aluminum tri-stearate, $(CH_3(CH_2)_{16}COO)_2$—Al—OH, an aluminum di-stearate, and an $CH_3(CH_2)_{16}COO$—Al(OH)$_2$, an aluminum mono-stearate.

Other examples of carboxylate metal salts include titanium stearates, tin stearates, calcium stearates, zinc stearates, boron stearate and strontium stearates. Non-limiting commercially available carboxylate metal salts for example include aluminum stearate commercially available from Chemtura Corporation, Memphis, Tenn.

The carboxylate metal salt in one embodiment may be combined with antistatic agents such as fatty amines, for example, KEMAMINE AS 990/2 zinc additive, a blend of ethoxylated stearyl amine and zinc stearate, or KEMAMINE AS 990/3, a blend of ethoxylated stearyl amine, zinc stearate and octadecyl-3,5-di-tert-butyl-4-hydroxyhydrocinnamate. Both these blends are available from Chemtura Corporation, Memphis, Tenn.

Commercially available carboxylate metal salts frequently contain free carboxylic acid or a derivative thereof, usually residually remaining after synthesis. Without being bound to theory, it is believed that flowability problems at ambient temperatures and above about 25° C. are due, at least in part, to the fraction of carboxylic acid or a derivative thereof having 14 carbon atoms or less, more particularly, aliphatic carboxylic acids or a derivative thereof having 14 carbon atoms or less.

In contrast, in several classes of embodiments, inventive continuity additives have no or are substantially free of a carboxylic acid or a derivative thereof having 14 carbon atoms or less, more particularly, aliphatic carboxylic acids or a derivative thereof having 14 carbon atoms or less. "Substantially free" preferably means that the metal carboxylate composition contains less than 5 wt %, more preferably less than 3 wt %, more preferably less than 2 wt %, more preferably less than 1.5 wt %, more preferably less than 1 wt %, more preferably less than 0.75 wt % and more preferably less than 0.5 wt % of a carboxylic acid or a derivative thereof having 14 carbon atoms or less. "Substantially free" may also refer to that fraction of a carboxylic acid or a derivative thereof having 14 carbon atoms or less required to depress the melting point (first melt) of an extracted (preferably with hexane) sample of a continuity additive by at least eight degrees (8° C.), alternatively, at least nine degrees (9° C.), alternatively, at least ten degrees (10° C.), alternatively, at least eleven degrees (11° C.), and alternatively, at least twelve degrees (12° C.) as shown in the Examples below. In another class of embodiments, "substantially free" refers to the catalyst system containing a continuity additive, such as the carboxylate metal salt, having no more than 7 wt % of a carboxylic acid or a derivative thereof having 14 carbon atoms or less based upon the total weight of the catalyst system, alternatively, having no more than 5 wt %, preferably no more than 4 wt %, preferably no more than 3 wt %, preferably no more than 2 wt %, preferably no more than 1 wt %, preferably no more than 0.75 wt %, preferably no more than 0.5 wt %, and preferably no more than 0.25 wt % of a carboxylic acid or a derivative thereof having 14 carbon atoms or less based upon the total weight of the catalyst system.

In some embodiments, a preferred metal carboxylate salt composition contains a hexane extractable fraction having a peak melting point in a DSC experiment of 60° C. or higher, more preferably 62° C. or higher, more preferably 63° C. or higher, more preferably 64° C. or higher, more preferably 65° C. or higher, more preferably 67° C. or higher and in some embodiments 70° C. or higher.

Thus, in several embodiments, without being bound by theory, it is believed that the poor flowability of catalyst compositions containing carboxylate metal salts at temperatures at ambient or above about 25° C. is associated with a low melting fraction present in commercially available carboxylate metal salts.

Catalyst Composition

The method for making the catalyst composition generally involves contacting the catalyst compound with the continuity additive compound. It is understood that contacting may also refer to combining, blending, mixing, or the like.

In one embodiment, a metallocene catalyst, optionally with other catalyst, is combined, contacted, blended, and/or mixed with a continuity additive. The catalyst may be supported. In another embodiment, the steps of the method include forming a catalyst, such as forming a supported catalyst, and contacting the catalyst with a continuity additive. In an illustrative embodiment, the catalyst composition may comprise a catalyst, an activator or cocatalyst, and a support.

One skilled in the art recognizes that depending on the catalyst system and the continuity additive compound used, certain conditions of temperature and pressure would be required to prevent, for example, a loss in the activity of the catalyst system.

In one embodiment, continuity additive is introduced directly into the reactor in the presence of a supported catalyst system. In another embodiment, the continuity additive is introduced directly into the reactor in the presence of catalyst system under ambient temperatures and pressures.

In alternative embodiment, introduction of the continuity additive directly into the reactor in the presence of a supported catalyst system may vary depending on one or more of the conditions, temperature and pressure, the type of mixing apparatus, the quantities of the components to be combined, and even the mechanism for introducing the catalyst/continuity additive combination into the reactor.

In a class of embodiments, the ratios of amount of continuity additive to the amount of polymer produced in the reactor at any time may be between 0.5 ppm and 1000 ppm, and between 1 ppm and 400 ppm in another embodiment, and between 5 ppm and 50 ppm in yet another embodiment.

Techniques and equipment contemplated for use in the method of the invention are understood. Mixing or contacting techniques may involve any mechanical mixing means, for example shaking, stirring, tumbling, and rolling. Another technique contemplated involves the use of fluidization, for example, in a fluid bed reactor vessel where circulated gases provide the contacting.

In one embodiment, a supported metallocene catalyst, is tumbled with a continuity additive for a period of time such that a substantial portion of the supported catalyst is mixed and/or substantially contacted with the continuity additive.

The continuity additive may also be pre-mixed with a cocatalyst or activator such as, an organo metallic compound, such as, MAO or MMAO, before being introduced into the reactor.

In another embodiment, the catalyst system is supported, preferably the supported catalyst system is substantially dried, preformed, and/or free flowing. In an embodiment, the preformed supported catalyst system is contacted with the continuity additive. The continuity additive may be in solution, emulsion, or slurry. It may also be in a solid form such as free flowing powder. In another embodiment, the continuity additive is contacted with a supported catalyst system, for example, a supported metallocene catalyst system, in a rotary mixer under a nitrogen atmosphere, most preferably the mixer is a tumble mixer, or in a fluidized bed mixing process.

In another illustrative embodiment, a metallocene catalyst, is contacted with a support to form a supported catalyst compound. In this embodiment, an activator for the catalyst compound is contacted with a separate support to form a supported activator. It is contemplated in this particular embodiment that a continuity additive is then mixed with the supported catalyst compound or the supported activator, in any order, separately mixed, simultaneously mixed, or mixed with only one of the supported catalyst, or preferably the supported activator prior to mixing the separately supported catalyst and activator.

In a class of embodiments, the mole ratio of the metal of the activator component to the metal of the metallocene catalyst compound is in the range of between 0.3:1 to 10,000:1, preferably 100:1 to 5000:1, and most preferably 500:1 to 2000:1.

In an embodiment, a method of co-injecting an unsupported catalyst and a continuity additive into the reactor is also provided. In one embodiment the catalyst is unsupported, for example, in a liquid form such as described in U.S. Pat. Nos. 5,317,036 and 5,693,727 and European publication EP-A-0 593 083. The catalyst in liquid form may be fed with a continuity additive to a reactor using the injection methods described, for example, in WO 97/46599.

Polymerization Processes

Polymerization processes may include solution, gas phase, slurry phase and a high pressure process or a combination thereof. In illustrative embodiments, a gas phase or slurry phase polymerization of one or more olefins at least one of which is ethylene or propylene is provided.

The catalysts and catalyst systems of the invention described above are suitable for use in any prepolymerization and/or polymerization process over a wide range of temperatures and pressures. The temperatures may be in the range of from −60° C. to about 280° C., preferably from 50° C. to about 200° C.; and from 60° C. to 120° C. in yet a more particular embodiment, and from 70° C. to 100° C. in yet another embodiment, and from 80° C. to 95° C. in yet another embodiment, wherein a desirable temperature range may include any combination of any upper limit with any lower limit described herein.

In one embodiment, the process of this invention is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefins or comonomers such as ethylene, propylene, 1-butene, 1-pentene, 4-methyl-1-pentene, 1-hexene, 1-octene 1-decene or the like.

Other olefins useful in the process of the invention include ethylenically unsaturated monomers, diolefins having 4 to 18 carbon atoms, conjugated or nonconjugated dienes, polyenes, vinyl monomers and cyclic olefins. Monomers useful in the invention may include, but are not limited to, norbornene, norbornadiene, isobutylene, isoprene, vinylbenzocyclobutane, styrenes, alkyl substituted styrene, ethylidene norbornene, dicyclopentadiene and cyclopentene.

In an illustrative embodiment of the process of the invention, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment of the process of the invention, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028, 670, 5,317,036, 5,352,749, 5,405,922, 5,436,304, 5,453,471, 5,462,999, 5,616,661 and 5,668,228)

The reactor pressure in a gas phase process may vary from about atmospheric pressure to about 600 psig in one embodiment; and from 100 psig (690 kPa) to about 500 psig (3448 kPa) in another embodiment, preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C.

Other gas phase processes contemplated by the process of the invention include those described in U.S. Pat. Nos. 5,627, 242, 5,665,818 and 5,677,375, and European publications EP-A-0 794 200, EP-A-0 802 202, EP-A2 0 891 990 and EP-B-634 421.

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

A polymerization technique of the invention is referred to as a particle form polymerization, or a slurry process where the temperature is kept below the temperature at which the polymer goes into solution. Such technique is well known in the art, and described in for instance U.S. Pat. No. 3,248,179. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

Examples of solution processes are described in U.S. Pat. Nos. 4,271,060, 5,001,205, 5,236,998 and 5,589,555.

Polymer Products

The polymers produced by the process of the invention can be used in a wide variety of products and end-use applications. The polymers produced by the process of the invention may include, but are not limited to, linear low density polyethylene, low density polyethylenes, and high density polyethylenes.

The polymers, including ethylene and propylene based polymers, have a density in the range of from 0.86 g/cm$^3$ to 0.97 g/cm$^3$, preferably in the range of from 0.88 g/cm$^3$ to 0.965 g/cm$^3$ and more preferably in the range of from 0.900 g/cm$^3$ to 0.96 g/cm$^3$.

The polymers produced by the process of the invention may have a molecular weight distribution, a weight average molecular weight to number average molecular weight (Mw/Mn) of greater than 1.5 to about 15, particularly greater than 2 to about 10 and more preferably greater than about 2.2 to less than about 8.

The polymers of the present invention in one embodiment may have a melt index (MI) or (I2) as measured by ASTM-D-1238-E (190/2.16) in the range from 0.01 dg/min to 1000 dg/min, more preferably from about 0.01 dg/min to about 100 dg/min and even more preferably from about 0.1 dg/min to about 100 dg/min.

The polymers of the invention in an embodiment may have a melt index ratio (I21/I2) (I21 is measured by ASTM-D-1238-F, [190/21.6]) of from 5 to 300, more preferably from about 10 to less than 250, and from 15 to 200 in yet another embodiment, and from 20 to 180 in yet another embodiment.

In yet another embodiment, propylene based polymers are produced in the process of the invention. These polymers may include, but are not limited to, atactic polypropylene, isotactic polypropylene, hemi-isotactic and syndiotactic polypropylene. Other propylene polymers may include propylene block or impact copolymers.

The polymers of the invention may be blended and/or coextruded with any other polymer. Non-limiting examples of other polymers include linear low density polyethylenes produced via conventional and/or single-site catalysis, elastomers, plastomers, high pressure low density polyethylene, high density polyethylenes, polypropylenes and the like.

Polymers produced by the process of the invention and blends thereof are useful in such forming operations as film, pipe, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers may include, are not limited to, melt spinning, solution spinning and melt blown fiber operations for use in woven or non-woven form to make filters, diaper fabrics, medical garments, geotextiles, etc. Extruded articles may include medical tubing, wire and cable coatings, geomembranes, and pond liners. Molded articles include single and multi-layered constructions in the form of bottles, tanks, large hollow articles, rigid food containers and toys, etc.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Example 1

Catalyst Preparation 575.7 kg (1268 lbs) of anhydrous toluene was charged into a stirred reactor a (reactor A). Thereafter, 481.24 kg (1060 lbs) of a 30 wt % methyl alumoxane (MAO) solution in toluene (Albemarle Corp., Baton Rouge, La.) was added to reactor A. The transfer lines were then rinsed with 49 kg (108 lbs) of toluene. While stirring the solution at ambient temperature, 41.8 (92 lbs) of a 25 wt % solution of bis-(1-methyl, 3-n-butylcyclopentadienyl) zirconium di-chloride was added. The vessel and transfer line were rinsed with 97.6 kg (216 lbs) of toluene. Mixing was continued for 60 minutes.

385.9 kg (850 lbs) of dehydrated grade 948 silica (W.R. Grace, Baltimore, Md.) was and charge into another vessel (reactor B). While stirring, the content of reactor A was slowly transferred into reactor B and rinsed with 136.2 kg (300 lbs) toluene. Mixing was allowed to continue at ambient temperature for 60 minutes. 27.2 kg (60 lbs) of a 10 wt % solution of KEMAMINE AS 990 in toluene (Ciba Corp.) was added to the mixture and stirring was continued at ambient temperature for 30 minutes. The vessel jacket temperature was then raised to 80° C. and the catalyst was dried to a free flowing solid. The resulting weight of the dried catalyst was approximately 558.4 kg (1230 lbs). Seven batches of catalyst were prepared as described in Example 1.

Examples 2

Preparation of Catalysts A, B and C

The catalyst as prepared in Example 1 was charged into a conical screw blender under anaerobic conditions and 13.6 kg (30 lbs) of a carboxylate metal salt, more particularly, aluminum stearate available from Chemtura Corporation, Memphis, Tenn., was added (hereinafter "comparative" continuity additive). The mixture was dry blended for a total of 18 minutes under low agitation speed after which it was discharged into a metal container and stored under nitrogen. The procedure was carried out three times to prepare catalysts A, B and C.

Example: 3

Preparation of Catalysts D, E, F, and G

The catalyst as prepared in Example 1 was charged into a conical screw blender under anaerobic conditions and 13.6 kg (30 lbs) of a carboxylate metal salt, more particularly, aluminum stearate that was synthesized using materials that had no or reduced amounts of carboxylic acids having 14 carbon atoms or less, more particularly, aliphatic carboxylic acids having 14 carbon atoms or less, available from Chemtura Corporation, Memphis, Tenn., was added (hereinafter "inventive" continuity additive). The mixture was dry blended for a total of 18 minutes under low agitation speed after which it was discharged into a metal container and stored under nitrogen. The procedure was carried out four times to prepare catalysts D, E, F, and G.

Example 4

Flowability Tests

A funnel test was used for measuring flow properties of the catalyst compositions. The following procedure outlines the steps followed to measure catalyst flowability. Because the catalyst samples A, B C, D, F and G are air and moisture sensitive, the test was performed under anaerobic conditions. The funnel was a glass funnel having a conical mouth with an opening angle of 60 degrees, a hole at the bottom and the funnel had no stem. The opening sizes of the funnel were 12, 10 and 7 mm. The steps were as follows:

1) Twenty grams of the catalyst sample was placed into a funnel whereby the bottom of the funnel was sealed.

2) To start the measurement, the bottom seal of the funnel was removed and the time for the entire catalyst to flow through the funnel was measured using a stopwatch.

3) The stopwatch time was recorded and the procedure repeated using a funnel having a smaller hole at the bottom with the exception that catalyst samples that did not flow through a certain size funnel were not tested using smaller size funnels.

The results of the flowability tests are presented in Table 1. The inventive blended catalyst generally exhibited better flow characteristics than the corresponding comparative blended catalysts.

TABLE 1

| | | Funnel Size | | |
| | | 12 mm | 10 mm | 7 mm |
| | | Time to pass funnel | | |
| Catalyst | Additive | (sec) | (sec) | (sec) |
| A | Comp. | 4 | 13 | 49 |
| B | Comp. | 7 | 13 | No Flow |
| C | Comp. | 6 | 11 | No Flow |
| D | Inventive | 5 | 10 | 38 |
| E | Inventive | 4 | 11 | 43 |
| F | Inventive | 3 | 9 | 36 |
| G | Inventive | 3 | 8 | 37 |

While not wishing to be bound by theory, the inventors offer the following explanation for the difference in flowability of the catalysts compositions. Carboxylate metal salts frequently contain free residual carboxylic acid. It is believed that flowability problems at ambient temperature and above about 25° C. are due, at least in part, to the fraction of residual carboxylic acid in the comparative samples such as aliphatic carboxylic acids having 14 carbon atoms or less. Inventive samples on the other hand were prepared with materials having no or reduced amounts of residual carboxylic acids having 14 carbon atoms or less.

Example 5

Extraction

The extraction of inventive and comparative samples was carried out according to the following procedure: 100 g of each sample was placed in a 1 liter bottle. 600 ml of isohexane was dehydrated over 4 A mol sieves and added to each sample to create a slurry. The slurry was stirred at room temperature for 8 hours and then filtered using a medium frit funnel. The solvent was evaporated from the filtrate and the solid residue was submitted for DSC analysis.

Example 6

Melting Behavior of the Extracts

DSC Measurements

DSC measurements were made on a Perkin Elmer System 7 Thermal Analysis System according to ASTM D 3418. For example, the data reported are $T_{max}$ from first melting data ($T_{max}$ first melt) and $T_{max}$ from second melting data ($T_{max}$ second melt), respectively. To obtain the $T_{max}$ first melt, a sample of reactor granules is heated at a programmed rate of 10° C./min to a temperature above its melting range. Specifically, the samples were 1) held for 10 min at −20° C., 2) heated from −20° C. to 200° C. at 10° C./min 3) held for 10 min at 200° C. To obtain the $T_{max}$ second melt, the sample is heated at a programmed rate of 10° C./min to a temperature above its melting range as described above, cooled at a programmed rate of 10° C./min to a temperature below its crystallization range (−20° C.), held at this low temperature for 10 min and reheated to 200° C. at a programmed rate of 10° C./min, where the data reported is from the first melt.

Figure 2:
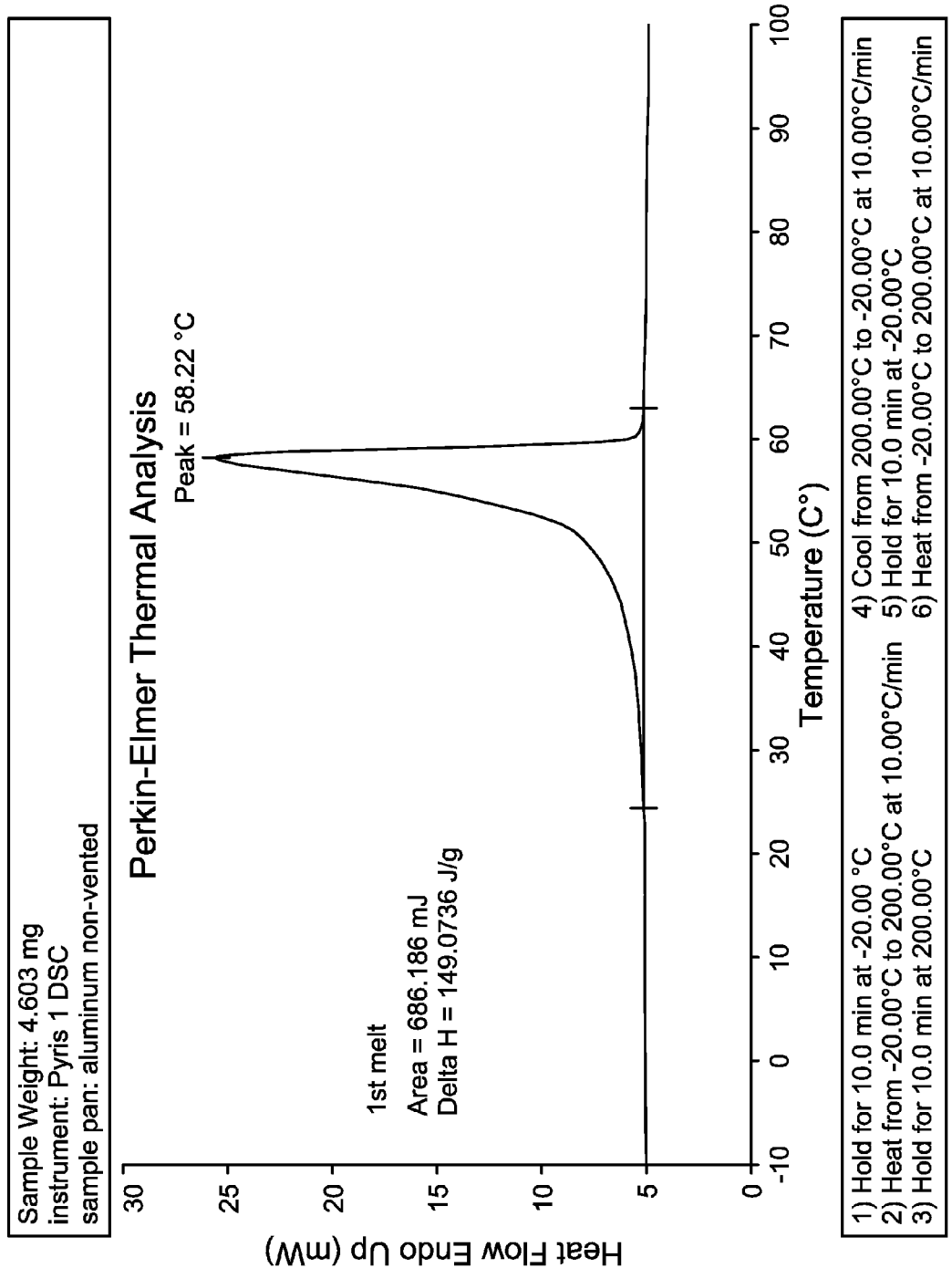
FIG. 2 presents differential scanning calorimetry results for the hexane extractable fraction of a comparative continuity additive as described more in the Examples below.

To illustrate the melting behavior of the hexane extracts of carboxylate metal salts, FIG. 1 shows the first melt DSC thermogram of the hexane extract of an inventive sample. FIG. 2 shows the melting behavior of a hexane extract of a comparative sample. The extract of the inventive sample has a peak melting point of approximately 68° C., which is about 10° C. higher than that of the comparative sample. The melting point of the comparative sample extract is approximately 58° C. corresponding a carboxylate metal salt having a fraction of a carboxylic acid having 14 carbon atoms or less. Thus, this difference in melt behavior, without wishing to be bound to theory, is accountable, at least in part, for the difference in flowability properties of the continuity additives, and in turn, the resulting catalyst composition incorporating such continuity additive.

Only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents cited are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A catalyst composition comprising a metallocene catalyst compound and a metal carboxylate salt, wherein 20 g of the catalyst composition at a temperature of 25° C. or higher flows through a funnel in less than 10 seconds, wherein the funnel is a glass funnel having a conical mouth with an opening angle of 60 degrees, a hole of 7 mm diameter at the bottom, and the funnel has no stem.

2. The catalyst composition of claim 1, wherein the catalyst composition at a temperature of 25° C. or higher flows through a funnel in less than 5 seconds, wherein the funnel is a glass funnel having a conical mouth with an opening angle of 60 degrees, a hole of 7 mm diameter at the bottom, and the funnel has no stem.

3. The catalyst composition of claim 1, wherein the catalyst composition at a temperature of 30° C. or higher flows through a funnel in less than 45 seconds, wherein the funnel is a glass funnel having a conical mouth with an opening angle of 60 degrees, a hole of 7 mm diameter at the bottom, and the funnel has no stem.

4. The catalyst composition of claim 1 wherein the metal carboxylate salt comprises a metal carboxylate salt composition according represented by the formula: MQ x(OOCR)$_y$, where M is a Group 2 or Group 13 metal from the Periodic table of Elements; Q is a halogen, hydroxy, alkyl, alkoxy, aryloxy, siloxy, silane or sulfonate group; R is a hydrocarbyl radical having from 14 to 100 carbon atoms; x is an integer from 0 to 3; y is an integer from 1 to 4; and the sum of x and y is equal to the valence of the metal M; wherein the carboxylate salt composition contains a hexane extractable fraction having a peak melting point in a DSC experiment of 65° C. or higher.

5. The catalyst composition according of claim 1, wherein the catalyst composition further comprises a support and an activator, and wherein the metallocene catalyst compound contains a titanium, zirconium, or hafnium atom.

6. The catalyst composition of any of claim 1, wherein the catalyst composition further comprises a support and an activator, and wherein the metallocene catalyst compound is selected from the group consisting of (Pentamethylcyclopentadienyl) (Propyl cyclopentadienyl) MX$_2$, Tetramethylcyclopentadienyl) (Propyl cyclopentadienyl) MX$_2$, (Tetramethylcyclopentadienyl) (Butyl cyclopentadienyl) MX$_2$, Me$_2$Si (Indenyl)$_2$MX$_2$, Me$_2$Si(Tetrahydroindenyl)$_2$MX$_2$, (n-propyl cyclopentadienyl)$_2$MX$_2$, (n-butyl cyclopentadienyl)$_2$MX$_2$, (1-Methyl, 3-Butyl cyclopentadienyl)$_2$MX$_2$, (Propyl cyclopentadienyl) (Tetramethylcyclopentadienyl) MX$_2$, (Butyl cyclopentadienyl)$_2$MX$_2$, (Propyl cyclopentadienyl)$_2$MX$_2$, and any combinations thereof, wherein M is Zr or Hf, and X is selected from the group consisting of F, Cl, Br, I, Me, CH$_2$SiMe$_3$, and C1 to C5 alkyls or alkenyls.

7. The catalyst composition of claim 1, wherein the metallocene catalyst compound is selected from the group consisting of (1-Methyl, 3-Butyl cyclopentadienyl)$_2$ZrX$_2$, and any combinations thereof, wherein X is selected from the group consisting of F, Cl, Br, I, and Me.

8. The catalyst composition of claim 1, wherein the weight percent of the metal carboxylate salt based on the total weight of the catalyst composition is in the range of from 0.5 weight percent to 5 weight percent.

9. The catalyst composition of claim 1, wherein the catalyst composition has no more than 7 wt % of a carboxylic acid or a derivative thereof having 14 carbon atoms or less based upon the total weight of the catalyst composition.

10. A catalyst composition comprising a catalyst compound selected from the group consisting of HN(CH2CH2N(2,4,6-Me3-Phenyl))$_2$MX$_2$ and HN(CH2CH2N(2,3,4,5,6-Me5-Phenyl))$_2$MX$_2$ and a metal carboxylate salt, wherein 20 g of the catalyst composition at a temperature of 25° C. or higher flows through a funnel in less than 10 seconds, wherein the funnel is a glass funnel having a conical mouth with an opening angle of 60 degrees, a hole of 7 mm diameter at the bottom, and the funnel has no stem.

* * * * *